United States Patent

Saxton et al.

[11] Patent Number: 5,527,520
[45] Date of Patent: Jun. 18, 1996

[54] METHOD OF MAKING A TITANIUM-CONTAINING MOLECULAR SIEVE

[75] Inventors: Robert J. Saxton, West Chester; John G. Zajacek, Devon, both of Pa.; Guy L. Crocco, Wilmington, Del.; Kanthi S. Wijesekera, Glen Mills, Pa.

[73] Assignee: ARCO Chemical Technology, L. P., Greenville, Del.

[21] Appl. No.: 420,187

[22] Filed: Apr. 11, 1995

Related U.S. Application Data

[60] Division of Ser. No. 329,732, Oct. 26, 1994, Pat. No. 5,453,511, which is a continuation-in-part of Ser. No. 302,554, Sep. 8, 1994, which is a division of Ser. No. 172,405, Dec. 23, 1993, Pat. No. 5,374,747.

[51] Int. Cl.$^6$ ........................................ C01B 37/00
[52] U.S. Cl. ........................ 423/706; 423/708; 423/713; 423/DIG. 27
[58] Field of Search ........................ 423/701, 706, 423/713, DIG. 27, 708

[56] References Cited

U.S. PATENT DOCUMENTS

| | | | |
|---|---|---|---|
| 4,410,501 | 10/1983 | Taramasso et al. | 423/705 |
| 4,539,193 | 9/1985 | Valyorsik . | |
| 4,554,145 | 11/1985 | Rubin | 423/706 |
| 4,576,805 | 3/1986 | Chang et al. | 423/715 |
| 4,642,226 | 2/1987 | Calvert et al. | 423/706 |
| 4,666,692 | 5/1987 | Taramasso et al. | 423/701 |
| 4,824,976 | 4/1989 | Clerici et al. | 549/531 |
| 4,828,812 | 5/1989 | McCullen et al. | 423/713 |
| 4,833,260 | 5/1989 | Neri et al. | 549/531 |
| 5,214,168 | 5/1993 | Zajacek et al. | 549/531 |
| 5,246,690 | 9/1993 | Bellussi et al. | 423/705 |
| 5,262,550 | 11/1993 | Crocco et al. | 549/531 |
| 5,310,534 | 5/1994 | Fajula et al. | 423/715 |
| 5,354,875 | 10/1994 | Nemeth et al. . | |
| 5,401,486 | 3/1995 | Mueller et al. | 423/713 |
| 5,474,754 | 12/1995 | Saxton et al. | 423/705 |

FOREIGN PATENT DOCUMENTS

| | | |
|---|---|---|
| 077522 | 4/1983 | European Pat. Off. . |
| 0311983 | 4/1989 | European Pat. Off. . |
| 2694549 | 8/1992 | France . |
| 2037596 | 6/1993 | Spain . |
| 8504856 | 11/1985 | WIPO . |
| 9402245 | 2/1994 | WIPO . |
| 9408898 | 4/1994 | WIPO . |
| 9412277 | 6/1994 | WIPO . |

OTHER PUBLICATIONS

Corma et al, *J. Catalysis* 145, 151–158 (1994) No month.
Kraushaar et al., *Catalysis Letters* L, 85–92 (1988) No month.
Schlögl, *Angen Chem. Int. Ed. Eng*, 32, (1993) No month.
Camblor et al., *Chem. Comm.* 8, 589–590 (1992) No month.
Thamgara, et al., *j. Catalysis* 130, 1–8(1991) No month.
Camblor et al., *Zeolites* 13, 82–87(1993) Feb..
Dartt et al., "Synthesis and Physiochemical . . .," Symposium on Chemically Modified Molecular Sieves, Div. Pet. Chem., 206th Annual ACS Meeting, 491–493(1993).
Lami et al., *Microporous Material*, 1, 237–244(1993) No month.
Ugiuna et al., *J. Chem. Soc., Chem. Commun.*, 27–28(1994) No month
Sato et al., *J. Chem. Soc., Chem. Commun.*, 1887–1888(1994) No month.
*J. Chem. Soc. Chem. Commun*, (1992) "A possible rok of Alkali metal Ions in the synthesis of Publ–Silica Molecular Sieves", Goepper et al. pp. 1665–1666 (No month).

*Primary Examiner*—Mark L. Bell
*Assistant Examiner*—David Sample
*Attorney, Agent, or Firm*—Stephen D. Harper

[57] ABSTRACT

A crystalline molecular sieve having a framework structure isomorphous with zeolite beta and containing Si and Ti, but essentially no framework Al, usefully catalyzes olefin epoxidation wherein hydrogen peroxide or an organic hydroperoxide is utilized as the oxidizing agent.

23 Claims, 3 Drawing Sheets

METHOD OF MAKING A TITANIUM-CONTAINING MOLECULAR SIEVE

This is a division of application Ser. No. 08/329,732, filed Oct. 26, 1994 now U.S. Pat. No. 5,453,511, which is a continuation-in-part of application Ser. No. 08/302,554, filed Sep. 8, 1994, which is a division of application Ser. No. 08/172,405, filed Dec. 23, 1993, now U.S. Pat. No. 5,374,747.

FIELD OF THE INVENTION

This invention relates to methods of selectively oxidizing olefins so as to obtain products containing epoxide functional groups. In particular, the invention pertains to processes whereby an active oxygen species such as an organic hydroperoxide or a hydrogen peroxide source is reacted with an ethylenically unsaturated substrate in the presence of a relatively large pore crystalline titanium-containing molecular sieve catalyst to yield an epoxide. The catalyst is characterized by a framework structure isomorphous to zeolite beta comprised of silica and titanium, but essentially free of framework aluminum.

BACKGROUND OF THE INVENTION

Many different methods for the preparation of epoxides have been developed. One such method involves the epoxidation of an olefin in a liquid phase reaction using an organic hydroperoxide as the oxidizing agent and certain solubilized transition metal compounds as catalyst. Although this approach is practiced commercially and generally provides high selectivity to epoxide, it has at least two characteristics which tend to limit process flexibility and increase production costs. The use of an organic hydroperoxide results in the generation of a co-product alcohol derived from the reacted hydroperoxide during epoxidation; approximately 1 equivalent of the co-product is obtained for each equivalent of epoxide. If no market exists for the alcohol, the co-product must either be further reacted (incurring additional processing costs) so as to convert it back to the hydroperoxide oxidant or to another compound for which a commercial demand exists. Recovery of the soluble metallic catalyst used in such a process for reuse in subsequent runs is also problematic. It would therefore be highly desirable to develop an insoluble (heterogeneous) epoxidation catalyst which has high activity and selectivity when utilized with an oxidant such as hydrogen peroxide which does not form an organic co-product. Such a catalyst would ideally be readily recoverable in active form from an epoxidation reaction mixture by filtration or similar separation techniques or be capable of being utilized in the form of a fixed bed or the like.

Workers at the Universidad Politecnica de Valencia have recently reported the synthesis of a titanium silicoaluminate isomorphous to zeolite beta (see Camblor et al., *J. Chem. Soc., Chem. Commun.* pp. 589–590 (1992), Camblor et al., *Zeolites* 13, pp. 82–87 (1993) and ES 2037596 (published Jun. 16, 1993)). Such aluminum-containing materials were found to catalyze the oxidation of alkanes to alcohols, ketones, and the like using hydrogen peroxide as the oxidant. This type of titanium silicoaluminate in unmodified (fully protonated) form is a poor catalyst for the production of epoxides from olefins, however [see Sato et al., *J. Chem Soc., Chem. Comm.* 1887–1888 (1994)].

SUMMARY OF THE INVENTION

We have now made the unexpected discovery that a crystalline titanium-containing molecular sieve characterized by a framework structure isomorphous to zeolite beta and comprised of Si and Ti atoms, but essentially free of framework aluminum, may be obtained by different synthetic routes. One route utilizes a combination of dealumination and titanium insertion steps, while another route employs a benzyl-substituted ammonium species. The molecular sieve selectively catalyzes the epoxidation of olefins using either an organic hydroperoxide or a source of hydrogen peroxide.

DETAILED DESCRIPTION OF THE INVENTION

Figure 1:
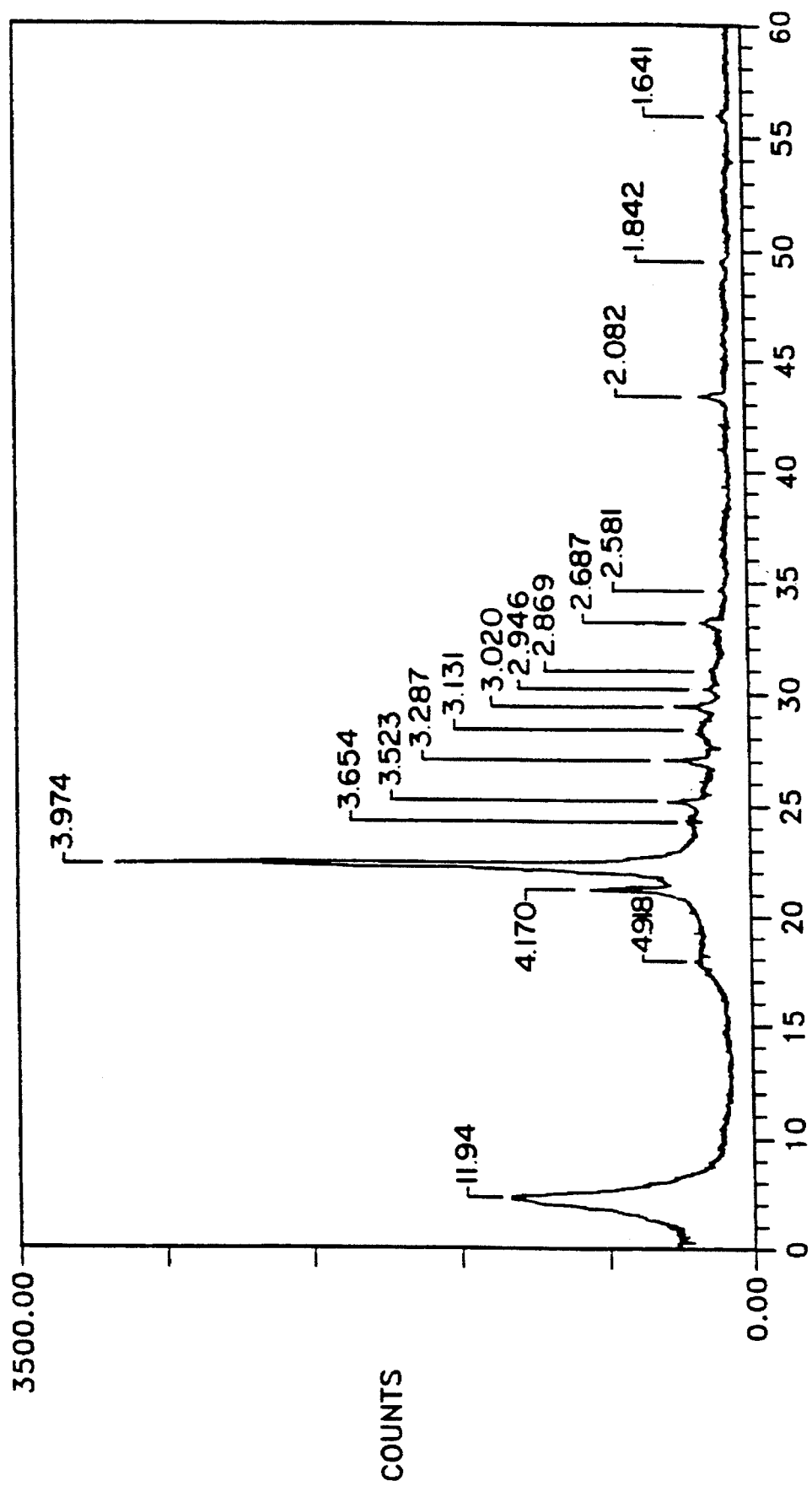
FIG. 1 is an X-ray powder diffraction pattern of the titanium-containing molecular sieve prepared using the procedure of Example 1.

In the epoxidation process of this invention, an olefin is contacted with an organic hydroperoxide or hydrogen peroxide (or a substance capable of producing an organic hydroperoxide or hydrogen peroxide under the reaction conditions) in the presence of a catalytically effective amount of a titanium-containing molecular sieve. The titanium-containing molecular sieve suitable for use is characterized by a framework structure isomorphous to zeolite beta. Si and Ti atoms are present in the framework structure (typically, in the form of oxides). The framework of the molecular sieve is essentially free of aluminum (Al), however; the presence of significant amounts of Al has been found to detrimentally affect the performance of said molecular sieve as an epoxidation catalyst unless the protons associated with aluminum are substituted with ammonium, alkali metal, or alkaline earth cations. In this context, "essentially free" means that the framework structure of the molecular sieve contains less than 1000 ppm Al. Preferably, less than 500 ppm Al is present in the framework structure. Most preferably, less than 100 ppm Al is present. The Si to Al molar ratio (Si:Al) is advantageously at least 750, more preferably at least 1000, but may be greater than 3000.

Zeolite beta is characterized by 12-member ring pore openings and a three dimensional interconnecting channel system; its framework structure is more completely described in U.S. Pat. No. 3,308,069, Szostak, *Handbook of Molecular Sieves*, pp. 92–96, Higgin et al., *Zeolites*, 8, 446 (1986), and Treacy et al., *Nature*, 332, 249 (1988). The catalyst of the invention thus has a fundamentally different structure than other titanium-containing molecular sieves reported in the prior art (e.g., the TS-1 catalyst described in U.S. Pat. No. 4,410,501, which has an MFI structure; the TS-2 catalyst described by Reddy et al. in *Appl. Cat.* 58, L1 (1990), which has a ZSM-11 structure; the all-silica Ti/ZSM-48 described by Serrano et al, *J. Chem. Commun.* 745 (1990)).

In preferred embodiments, the titanium-containing molecular sieve has relatively large pores (equal to or greater than about 6 angstroms on average) and has a zeolite-type structure comprised of Si and a lesser amount of Ti. A crystallinity of greater than 75% is usually desirable; the synthetic methods described herein are capable of providing crystallinities exceeding 95%. Preferably, the molar ratio of Ti:Si is from 0.1:99.9 to 20:80, with ratios in the range of 1:99 to 15:85 being especially preferred. The titanium-containing molecular sieve advantageously may have a titanium content of from 1 to 10 weight percent.

The general formula for the titanium-containing molecular sieve is preferably as follows:

$SiO_2:yTiO_2$ wherein y is from 0.01 to 0.25 (preferably, 0.02 to 0.20).

Preferred methods for synthesizing the essentially Al-free titanium-containing molecular sieves which are the subject of this application involve the use of a benzyl-substituted ammonium species. Without wishing to be bound by theory, it is believed that the benzyl-substituted ammonium species may function as a template for directing the assemblage of the required zeolite beta lattice framework from reactants which serve as sources of Si and Ti, but could also be accomplishing the desired synthetic result by acting as a buffer or structure-directing agent. The use of the term "template" herein is not meant to indicate that the benzyl-substituted ammonium species is in fact participating in a templating mechanism. The use of a benzyl-substituted ammonium species to prepare the catalysts of the present invention is advantageous since such a method tends to furnish molecular sieves which are less acidic, have less extra-framework Ti (e.g., anatase), and contain fewer defect sites than those obtained by the dealumination/insertion method to be described hereafter. It has been unexpectedly discovered that only benzyl-substituted ammonium species are capable of properly functioning as templates for this purpose; the tetraalkyl ammonium species such as tetraethyl ammonium salts conventionally employed as templates in the synthesis of other titanium-containing molecular sieves fail to provide highly crystalline products of high purity. Without wishing to be bound by theory, it is believed that the criticality of the type of template used is due to the absence of any aluminum species in such syntheses. The beta structure is thought to be an unstable, kinetic phase which crystallizes only under very specific conditions. This contrasts with the relative ease with which molecular sieves having an MFI structure (e.g., TS-1, ZSM-5, silicalite) may be prepared by template-directing techniques; such materials may be crystallized using a wide variety of templates.

Suitable benzyl-substituted ammonium species include quaternary ammonium compounds containing at least one nitrogen atom substituted with a benzyl group

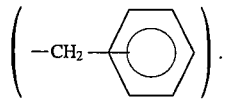

Preferably, each nitrogen bears only a single benzyl group, with the other groups attached to nitrogen being preferably alkyl groups (efforts to use dibenzyldimethyl ammonium hydroxide as a template, for example, have to date been unsuccessful).

Preferred benzyl-substituted ammonium species useful as templates in the synthesis of Al-free titanium-containing molecular sieves having a zeolite beta structure include diquaternary compounds having two nitrogen atoms within the same molecule wherein each nitrogen atom bears four hydrocarbon substituents with one substituent being a benzyl group. The nitrogen atoms are linked by an organic moiety which may be aliphatic (straight chain, branched, cyclic), aromatic or both aliphatic and aromatic in character. Preferably, the nitrogen atoms are separated by at least two, but no more than sixteen, carbon atoms. In a particularly preferred embodiment, the template is a 4,4'-trimethylene bis (N-benzyl N-methyl piperidinium) species having the structure

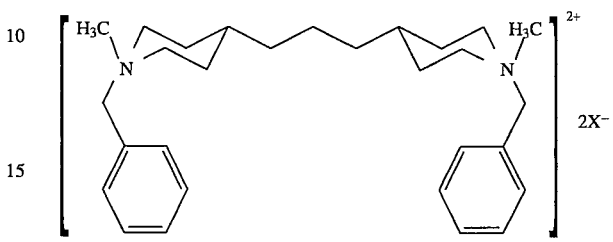

wherein X is preferably halide (e.g., Br) or hydroxide (OH).

In one method whereby a benzyl-substituted ammonium species may be used as a template to synthesize the molecular sieve which is the object of this invention, a solubilized partial hydrozylate is generated by reacting a hydrolyzable silicon compound and a hydrolyzable titanium compound with water under acidic conditions. "Hydrolyzable" in this context means that the compound is capable of functioning as a source of the $SiO_2$ or $TiO_2$ moieties in the framework of the crystalline titanium-containing molecular sieve upon reaction with water. Although such hydrolysis reaction may be performed in any order, it is preferred to first contact the hydrolyzable silicon compound with water prior to hydrolysis of the hydrolyzable titanium compound.

The hydrolyzable silicon compound may be any substance capable of functioning as a source of $SiO_2$ (silica) including, for example, amorphous or fumed silica or, more preferably, a tetraalkoxysilane such as tetraethyl orthosilicate or the like. Suitable hydrolyzable titanium compounds am those species which serve as a source of $TiO_2$ (titania) such as titanium halide (e.g., $TiCl_4$) or, more preferably, a titanium alkoxide such as titanium tetrabutoxide or the like.

The partial hydrolysis of the above-described reactants is catalyzed by an acidic catalyst such as, for example, a mineral acid or organic acid. Most preferably, a dilute (<0.2M) mineral acid such as hydrochloric acid is utilized. The partial hydrolysis may be carried out in any solvent capable of dissolving the partial hydrolyzate which is formed. In a particularly desirable embodiment, water and/or a lower aliphatic alcohol such as ethanol or isopropanol is employed as a hydrolysis solvent. Hydrolysis temperatures are selected so as to achieve partial hydrolysis without over-hydrolysis, since over-hydrolysis may generate insoluble $SiO_2$ and/or $TiO_2$ species. Temperatures of from 0° C. to 50° C. are generally suitable for this purpose. The water is contacted with the aforedescribed reactants for a time (typically, from 0.5 to 12 hours) sufficient to form a solubilized partial hydrozylate which is characterized by the absence of precipitated silicon dioxide and titanium dioxide. Although the precise structure of the solubilized partial hydrozylate is not known, it is believed to comprise an extended network of Si and Ti atoms interconnected by bridging oxygen atoms which contains sufficient non-oxygen substituents on the Si and Ti atoms such as alkoxy groups and the like to render the network soluble in the hydrolysis medium.

The solubilized partial hydrozylate is thereafter treated with a catalytic amount of the benzyl-substituted ammonium species effective to accomplish further hydrolysis such that a solid amorphous SiO$_2$—TiO$_2$ cogel is formed. Sufficient benzyl-substituted ammonium species must be present to both neutralize the acid and to render the hydrolysis medium basic. The cogel generally precipitates from the hydrolysis medium and may be recovered by any suitable means such as filtration, centrifugation, decantation, or the like. For reasons which are not fully understood, it has been found that the use of a benzyl-substituted ammonium species rather than another type of base such as ammonia facilitates the successful preparation of a crystalline Al-free titanium-containing molecular sieve having a zeolite beta structure. Hydrolysis of the solubilized partial hydrozylate leads to the formation of a solid amorphous SiO$_2$—TiO$_2$ cogel. The cogel may be taken on directly to template impregnation or, if so desired, may be separated from any remaining liquid components (e.g., solvent) by drying, filtration, or other such methods.

The solid cogel is contacted with a solution of the benzyl-substituted ammonium species in a solvent to form an impregnated cogel such that the template is preferably contained substantially within the pores of the cogel. The total amount of benzyl-substituted ammonium species in the hydrolysis and impregnation steps is preferably within 50% (more preferably, 20%) of the amount needed to fill the available pore volume of the cogel. At the same time, the amount of solvent (which preferably is a polar species such as water and/or alcohol) is preferably sufficient to dissolve the benzyl-substituted ammonium species but is not large enough to form a slurry of the cogel in said solvent (i.e., a free-flowing pumpable suspension of the cogel in the liquid solvent). Wetness impregnation techniques may be advantageously employed for such purpose. The solid cogel and benzyl-substituted ammonium species solution are contacted for a time and at a temperature sufficient to allow the template to enter the cogel pores (typically, 0.25 hours to 24 hours at 0° C. to 50° C.). The impregnated cogel is then heated at a temperature of from 120° C. to 160° (more preferably, 130° C. to 140° C.) for a time effective to form the desired titanium-containing molecular sieve. Generally speaking, from 1 to 14 days will be sufficient to provide high yields of product. It is preferred that the impregnated cogel not be stirred or otherwise agitated during heating.

The relative proportions of the various reactants used to prepare the impregnated cogel may be varied as desired so as to favorably influence the elemental composition of the final titanium-containing molecular sieve. The composition of the impregnated cogel in terms of molar ratios where the benzyl-substituted ammonium species is a diquaternary species may be as follows:

| | |
|---|---|
| SiO$_2$/TiO$_2$ | 5–200, preferably 10–100 |
| X$^-$/SiO$_2$ | 0.002–1, preferably 0.05–0.6 |
| H$_2$O/SiO$_2$ | 0.1–10, preferably ca. 1–5 |
| M$^+$/SiO$_2$ | 0–0.5, preferably ca. 0 |
| DQ$^{2+}$/SiO$_2$ | 0.005–2.0, preferably 0.025–1.0 | where M$^+$ is an alkali metal cation such as Na$^+$ or K$^+$ (preferably, no alkali metal cation is purposefully added), DQ$^{2+}$ is the dication portion of the diquaternary ammonium species, and X$^-$ is the anion associated with the diquaternary ammonium species (preferably Br$^-$ or OH$^-$).

The titanium-containing molecular sieve of this invention may alternatively be prepared using the benzyl-substituted ammonium species in a solution-type synthesis. This method comprises forming a mixture, preferably in solution, of a hydrolyzable silicon compound, a hydrolyzable titanium compound, and the benzyl-substituted ammonium species, and subjecting said mixture to hydrothermal treatment at a temperature of from 100° to 200° C. (more preferably, 120° to 180° C.) for a time effective to form the crystalline titanium-containing molecular sieve. Such hydrothermal treatment is most preferably conducted in an aqueous medium (which may, in addition to water, contain a water-miscible organic solvent such as an alcohol) under conditions such that hydrolysis of the silicon and titanium compounds is achieved. Hydrolysis may be catalyzed by base, if so desired. Any of the hydrolyzable silicon compounds, hydrolyzable titanium compounds and benzyl-substituted ammonium species previously described may be utilized for such purpose. Where a diquaternary compound is utilized as the benzyl-substituted ammonium species, the starting reagents may, for example, have the following preferred molar ratios:

| | |
|---|---|
| SiO$_2$/TiO$_2$ | 5–2000 |
| X$^-$/SiO$_2$ | 0.1–2.0 |
| H$_2$O/SiO$_2$ | 20–200 |
| DQ$^{2+}$/SiO$_2$ | 0.1–2.0 | wherein X$^-$ is the anion associated with the diquaternary ammonium species and DQ$^{2+}$ is the dication associated with the diquaternary ammonium species. A suitable preferred procedure for accomplishing formation of the mixture is as follows: partial hydrolysis of the hydrolyzable silicon compound is first carried out by reacting said compound with water containing a portion of the benzyl-substituted ammonium species (in hydroxide form). The partial hydrolysis product thereby obtained is then combined with the hydrolyzable titanium compound (and, optionally, an additional amount of the hydrolyzable silicon compound). The remaining amount of the benzyl-substituted ammonium species is thereafter added to yield a precursor gel. Any volatile co-products generated as a result of hydrolysis (such as, for example, alcohols where the hydrolyzable silicon compound is a tetraalkyl orthosilicates or where the hydrolyzable titanium compound is a titanium tetraalkoxide) may, if desired, be removed by any suitable means such as distillation or evaporation prior to hydrothermal treatment. The hydrothermal treatment is advantageously performed in an autoclave or other closed reactor under autogenous pressure. Typically, a period of from 3 to 20 days is sufficient to form the titanium-containing molecular sieve in crystalline, precipitated form. In general, optimum results are obtained using a hydrothermal treatment time of about fourteen days. Such crystals, which will generally contain the benzyl-substituted ammonium species template, may be separated from the mother liquor by suitable means such as filtration, decantation, or centrifugation, washed with a suitable liquid medium such as water, then dried.

The crystalline product obtained by the above-described techniques involving a benzyl-substituted ammonium species template may, if so desired, be calcined in air or the like at a temperature in excess of 400° C. in order to remove the template still present within the pores of the molecular sieve.

An alternative suitable method for the preparation of the aforedescribed titanium-containing molecular sieves involves a procedure wherein zeolite beta is dealuminated and the framework vacancies created by dealumination filled by titanium atoms. This method is relatively rapid and can provide high yields of active catalyst, as compared to, for example, hydrothermal techniques which can require 1 week or more per batch and which may provide lower yields of catalyst. Post-synthesis dealumination methods are well-known and include, for example, reaction or leaching with mineral acids (e.g., HCl, H$_2$SO$_4$, HNO$_3$) or chelating agents and hydrothermal or steaming treatments (possibly combined with acid leaching). See, for example, the extensive listing of publications describing zeolite dealumination methods catalogued in U.S. Pat. No. 4,576,805 (col. 8, line 62 through col. 9, line 27) and Scherzer, "The Preparation and Characterization of Aluminum-Deficient Zeolites", *ACS Symp. Ser.* 248, 157–200 (1984). A particularly preferred method employs treatment of zeolite beta with a mineral acid such as nitric acid (preferably, 2 to 13M; most preferably, concentrated nitric acid) at a temperature of from 25° C. to 150° C. for a period of time of from 5 minutes to 24 hours. Other mineral acids and carboxylic acids could alternatively be used, as described, for example, in British Pat. No. 1,061,847, European Pat. Publication No. 488,867, Kraushaar et al., *Catalysis Letters* 1, 81–84 (1988), Chinese Pat. No. 1,059,701 (*Chem. Abst.* 117:114655g), European Pat. Publication No. 95,304, and Chinese Pat. No. 1,048,835 (*Chem. Abst.* 115: 52861u). The beta zeolite is desirably suspended in or otherwise contacted with a relatively large volume of the nitric acid (preferably, from 10 to 1000 parts by weight nitric acid per 1 part by weight of the zeolite beta). Multiple dealuminations of this sort may be performed to effect more complete Al removal. Suitable dealumination methods of this type are described in more detail in Lami et al., *Microporous Materials* 1, 237–245 (1993) and European Pat. Publication No. 488,867. The dealuminated material may thereafter be contacted with a titanium source. For example, the dealuminated zeolite beta may be exposed to a volatile titanium source such as $TiCl_4$ vapor in nitrogen for 1 to 24 hours at an elevated temperature (preferably, 250° C. to 750° C.). A liquid phase source of titanium such as $(NH_4)_2TiF_6$ (aq.) or $TiF_4$ (aq.) may alternately be utilized to insert Ti atoms into the framework vacancies of the dealuminated zeolite beta. Also suitable for use are solid sources of titanium which can be vaporized at accessible temperatures such as, for example, titanium alkoxides (e.g., $Ti(OMe)_4$). Methods of post-synthesis titanium incorporation into zeolite materials are described, for example, in U.S. Pat. No. 4,576,805, U.S. Pat. No. 4,828,812, and Kraushaar, et al., *Catal. Lett.* 1, 81–84 (1988). It may be desirable to then treat the titanium-containing molecular sieve with an ammonium salt such as ammonium nitrate, an acid solution (such as aqueous nitric acid) or the like to convert the titanium source to acid form (i.e., hydrogen or hydronium form) or to remove extra-framework aluminum. Water-washing, drying, and/or calcination may also be advantageous.

As a consequence of their extremely low Al content, the titanium-containing molecular sieves of this invention are typically low in acidity. However, to further enhance the performance of certain titanium-containing molecular sieves prepared as described hereinabove, it may be advantageous to contact the catalyst with an ammonium, alkali metal and/or alkaline earth metal compound. Without wishing to be bound by theory, it is believed that this enhancement may be attributable to the neutralization of certain metal-associated acidic sites present in the titanium-containing molecular sieve. A preferred method for accomplishing this modification is to dissolve the ammonium, alkali metal or alkaline earth metal compound in water or other suitable liquid medium; the resulting solution is then brought into intimate contact with the molecular sieve. This procedure preferably is performed at a temperature sufficiently high so as to accomplish the partial (i.e., at least 25%) or complete exchange or replacement of the ammonium, alkali metal or alkaline earth metal for the hydrogen cations of the acidic sites within a practicably short period of time (e.g., within 24 hours). For this purpose, temperatures of from about 25° C. to 150° C. will generally suffice. The concentration of ammonium, alkali metal or alkaline earth metal compound in the liquid medium may be varied as desired and will typically be from about 0.001 to 5 molar. Optimum concentrations may be readily ascertained by routine experimentation. Following the desired cation exchange, the excess liquid medium may be separated from the titanium-containing molecular sieve by filtration, decantation, centrifugation, or other such technique, and the modified titanium-containing molecular sieve washed (if desired) with water or other liquid substance, and then dried and/or calcined prior to use in the epoxidation process of this invention. If an ammonium compound has been utilized, calcination is preferably avoided so as to minimize any re-protonation of the catalyst.

The particular ammonium, alkali metal or alkaline earth metal compound selected for use is not critical but preferably is water-soluble and is desirably selected from ammonium, alkali metal or alkaline earth metal hydroxides and oxides (e.g., sodium hydroxide, potassium hydroxide, barium hydroxide, calcium hydroxide), ammonium, alkali metal or alkaline earth metal carbonates (e.g., sodium carbonate, potassium carbonate), ammonium, alkali metal or alkaline earth metal bicarbonates (e.g., sodium bicarbonate, potassium bicarbonate), ammonium, alkali metal or alkaline earth metal nitrates (e.g., sodium nitrate, potassium nitrate), ammonium, alkali metal or alkaline earth metal halides (e.g., potassium chloride, sodium bromide, sodium chloride), ammonium, alkali metal or alkaline earth metal sulfates (e.g., sodium sulfate, potassium sulfate), ammonium, alkali metal or alkaline earth metal salts of carboxylic acids (e.g., sodium acetate), and the like and mixtures thereof. The counter-anion in the ammonium, alkali metal or alkaline compound should be chosen such that it does not interfere with the desired activity of the titanium-containing molecular sieve nor detrimentally alter its crystalline structure. For example, it has been found that under certain conditions the use of alkali metal pyrophosphates may deactivate or poison the molecular sieve catalyst.

In one embodiment of the invention, an ammonium, alkali metal, or alkaline earth-modified titanium-containing molecular sieve is generated in-situ during epoxidation through the use of an unmodified titanium-containing molecular sieve in combination with either an ammonium, alkali metal or alkaline earth compound of the type described previously or a buffer comprised of an ammonium, alkali metal or alkaline earth salt of a carboxylic acid or the like. For example, the reaction medium wherein the olefin is contacted with hydrogen peroxide may contain a NaOAc/HOAc buffer system (preferably, 0.1 to 5M) in a suitable solvent such as an alcohol (e.g., methanol). Alternatively, an alkali metal compound alone such as sodium acetate could be utilized. In a batch process, the ammonium, alkali metal or alkaline earth compound could, for example, be added by itself prior to initiation of epoxidation while in a continuous process (as when a CSTR reactor is employed) such compound could be combined with one of the feed streams containing one of the other reaction components such as the oxidizing agent.

The surface acidity of the titanium-containing molecular sieve may alternatively be advantageously reduced by silylation. Silylation may be accomplished, for example, by reacting with chlorotrimethyl silane or the like.

The amount of catalyst employed to epoxidize an olefin is not critical, but should be sufficient so as to substantially accomplish the desired reaction in a practicably short period of time. The optimum quantity of catalyst will depend upon a number of factors including reaction temperature, olefin reactivity and concentration, oxidizing agent concentration, type and concentration of organic solvent as well as catalyst activity. Typically, however, in a batch type epoxidation, the amount of catalyst will be from 0.001 to 10 grams per mole of olefin. In a fixed bed system, the optimum quantity of catalyst will be influenced by the flow of reactants through the fixed bed (typically, from about 1 to 100 moles oxidizing agent per kilogram of catalyst per hour). The concentration of titanium in the total epoxidation reaction mixture will generally be from about 10 to 10,000 ppm.

The catalyst may be utilized in powder, pellet, microspheric, monolithic, extruded, or any other suitable physical form. The use of a binder (co-gel) or support in combination with the titanium-containing molecular sieve may be advantageous. Supported or bound catalysts may be prepared by the methods known in the art to be effective for zeolite catalysts in general. For example, the catalyst may be supported on titania by adaptation of the techniques described in U.S. Pat. No. 5,354,875.

Illustrative binders and supports (which preferably are non-acidic in character) include silica, alumina, silica-alumina, silica-titania, silica-thoria, silica-magnesia, silica-zironia, silica-beryllia, and ternary compositions of silica with other refractory oxides. Also useful are clays such as montmorillonites, kaolins, bentonites, halloysites, dickites, nacrites, and anaxites. The proportion of titanium-containing molecular sieve to binder or support may range from 99:1 to 1:99, but preferably is from 5:95 to 80:20. The catalyst may also be impregnated or admixed with a noble metal such as Pt, Pd, or the like.

The olefin substrate epoxidized in the process of this invention may be any organic compound having at least one ethylenically unsaturated functional group (i.e., a carbon-carbon double bond) and may be a cyclic, branched or straight chain olefin. The olefin may contain aryl groups (e.g., phenyl, naphthyl). Preferably, the olefin is aliphatic in character and contains from 2 to 30 carbon atoms (i.e., a $C_2$–$C_{30}$ olefin). The use of light (low-boiling) $C_2$ to $C_{10}$ mono-olefins is especially advantageous. More than one carbon-carbon double bond may be present in the olefin; dienes, trienes, and other polyunsaturated substrates thus may be used. The double bond may be in a terminal or internal position in the olefin or may alternatively form part of a cyclic structure (as in cyclohexene, for example). Other examples of suitable substrates include unsaturated fatty acids or fatty acid derivatives such as esters or glycerides and oligomeric or polymeric unsaturated compounds such as polybutadiene. Benzylic and styrenic olefins may also be epoxidized, although the epoxides of certain styrenic olefins such as styrene may further react or isomerize under the conditions utilized in the present invention to form aldehydes and the like.

The olefin may contain substituents other than hydrocarbon substituents such as halide, carboxylic acid, ether, hydroxy, thiol, nitro, cyano, ketone, acyl, ester, anhydride, amino, and the like.

Exemplary olefins suitable for use in the process of this invention include ethylene, propylene, the butenes (e.g., 1,2-butene, 2,3-butene, isobutylene), butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, styrene (and other vinyl aromatic substrates) polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinyl cyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triglyceride esters) and the like.

Mixtures of olefins may be epoxidized and the resulting mixtures of epoxides either employed in mixed form or separated into the different component epoxides.

The process of this invention is especially useful for the epoxidation of $C_2$–$C_{30}$ olefins having the general structure

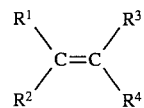

wherein $R^1$, $R^2$, $R^3$, and $R^4$ are the same or different and are selected from the group consisting of hydrogen and $C_1$–$C_{20}$ alkyl.

The oxidizing agent employed in the process of this invention may be either a hydrogen peroxide source such as hydrogen peroxide ($H_2O_2$) or an organic hydroperoxide or a compound which under the epoxidation reaction conditions is capable of generating or liberating hydrogen peroxide or an organic hydroperoxide. For reasons which are not yet fully understood, it has been found that epoxidation may often be more readily accomplished (i.e., higher reaction rates, higher epoxide selectivity) using organic hydroperoxide as oxidizing agent. This result was quite unexpected in view of a recent report [Khouw et al., *J. Catalysis* 149, 195–205 (1994)] that other aluminum-free titanium-containing ZSM-5 molecular sieves ("TS-1") are inactive as oxidation catalysts using organic hydroperoxides and that the inactivity is not due to the relatively small pore size of the TS-1 but rather to the steric bulk of organic hydroperoxides when complexed to the active Ti sites.

The amount of oxidizing agent relative to the amount of olefin is not critical, but most suitably the molar ratio of oxidizing agent:olefin is from 100:1 to 1:100 when the olefin contains one ethylenically unsaturated group. The molar ratio of ethylenically unsaturated groups in the olefin substrate to oxidizing agent is more preferably in the range of from 1:10 to 10:1. One equivalent of oxidizing agent is theoretically required to oxidize one equivalent of a mono-unsaturated olefin substrate, but it may be desirable to employ an excess of one reactant to optimize selectivity to the epoxide.

Although the hydrogen peroxide which may be utilized as the oxidizing agent may be derived from any suitable source, a distinct practical advantage of the process of this invention is that the hydrogen peroxide may be obtained by contacting a secondary alcohol such as alpha-methyl benzyl alcohol, isopropyl alcohol, 2-butanol, or cyclohexanol with molecular oxygen under conditions effective to form an oxidant mixture comprised of secondary alcohol and hydrogen peroxide (and/or hydrogen peroxide precursors). Typically, such an oxidant mixture will also contain a ketone such as acetophenone, acetone, or cyclohexanone corresponding to the secondary alcohol (i.e., having the same carbon skeleton), minor amounts of water, and varying amounts of other active oxygen species such as organic hydroperoxides.

Molecular oxygen oxidation of anthrahydroquinone, alkyl-substituted anthrahydroquinones, or water-soluble anthrahydroquinone species may also be employed to generate the hydrogen peroxide oxidant. The hydrogen peroxide may be generated in situ immediately prior to or simultaneous with epoxidation, as described, for example, in European Pat. Publication No. 526,945, Japanese Kokai No. 4-352771, Ferrini et al., "Catalytic Oxidation of Alkanes Using Titanium Silicate in the Presence of In-Situ Generated Hydrogen Peroxide", DGMK Conference on Selective Oxidations in Petrochemistry, Sep. 16–18, 1992, pp. 205–213, and European Pat. Pub. No. 469,662.

The organic hydroperoxides usable as the oxidizing agent in the epoxidation process of this invention may be any organic compound having at least one hydroperoxy functional group (—OOH). Secondary and tertiary hydroperoxides are preferred, however, owing to the higher instability and greater safety hazards associated with primary hydroperoxides. The organic hydroperoxide preferably has the general structure:

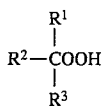

wherein $R^1$, $R^2$ and $R^3$ are the same or different and are selected from the group consisting of hydrogen, $C_1$–$C_{10}$ alkyl (e.g., methyl, ethyl, t-butyl) and $C_6$–$C_{12}$ aryl (e.g. phenyl, alkyl substituted phenyl), subject to the proviso that not more than one of $R^1$, $R^2$, or $R^3$ is hydrogen. Exemplary organic hydroperoxides include t-butyl hydroperoxide, t-amyl hydroperoxide, cumene hydroperoxide, ethyl benzene hydroperoxide, cyclohexyl hydroperoxide, methyl cyclohexyl hydroperoxide, tetralin hydroperoxide, isobutyl benzene hydroperoxide, ethyl naphthalene hydroperoxide, and the like. Mixtures of organic hydroperoxides may also be employed.

If desired, a solvent may additionally be present during the epoxidation process of this invention in order to dissolve the reactants other than the titanium-containing molecular sieve catalyst, to provide better temperature control, or to favorably influence the epoxidation rates and selectivities. The solvent, if present, may comprise from 1 to 99 weight percent of the total epoxidation reaction mixture and is preferably selected such that it is a liquid at the epoxidation reaction temperature. Organic compounds having boiling points at atmospheric pressure of from about 25° C. to 300° C. are generally preferred for use. Excess olefin may serve as a solvent or diluent. Illustrative examples of other suitable solvents include, but are not limited to, ketones (e.g., acetone, methyl ethyl ketone, acetophenone), ethers (e.g., tetrahydrofuran, butyl ether), nitriles (e.g., acetonitrile), aliphatic and aromatic hydrocarbons, halogenated hydrocarbons, and alcohols (e.g., methanol, ethanol, isopropyl alcohol, t-butyl alcohol, alpha-methyl benzyl alcohol, cyclohexanol, trifluoroethanol). The use of a polar but weakly coordinating solvent such as trifluoroethanol has been found to enhance catalyst activity and selectivity, particularly where the oxidant is an organic hydroperoxide such as TBHP. An important practical advantage of the present invention is that it may readily be practiced using bulkier alcohol solvents such as alpha-methyl benzyl alcohol, whereas poor results are obtained with such solvents when other titanium-containing molecular sieves such as TS-1 are utilized as catalyst. This flexibility minimizes the problems which might otherwise be encountered when trying to separate the epoxide product from the epoxidation reaction mixture. Quantitative removal of methanol, for example, from a relatively light epoxide such as propylene oxide is difficult due to the similarity in their boiling points. More than one type of solvent may be utilized. Water may also be employed as a solvent or diluent; surprisingly, the process of the invention proceeds with minimal hydrolysis even when a significant quantity of water is present in the epoxidation reaction mixture. Biphasic as well as monophasic reaction systems thus are possible using the present invention.

The reaction temperature is not critical, but should be sufficient to accomplish substantial conversion of the olefin to epoxide within a reasonably short period of time. It is generally advantageous to carry out the reaction to achieve as high a conversion of oxidizing agent as possible, preferably at least 50%, more preferably at least 90% most preferably at least 95%, consistent with reasonable selectivities. The optimum reaction temperature will be influenced by catalyst activity, olefin and oxidizing agent reactivity, reactant concentrations, and type of solvent employed, among other factors, but typically will be in a range of from about 0° C. to 150° C. (more preferably, from about 25° C. to 120° C.). Reaction or residence times of from about 1 minute to 48 hours (more desirably, from about 10 minutes to 8 hours) will typically be appropriate, depending upon the above-identified variables. Although subatmospheric pressures can be employed, the reaction is preferably (especially when the boiling point of the olefin is below the epoxidation reaction temperature) performed at atmospheric pressure or at elevated pressure (typically, between 1 and 100 atmospheres). Generally, it will be desirable to pressurize the epoxidation vessel sufficiently maintain the reaction components as a liquid phase mixture. For example, performing the epoxidation at elevated pressure will increase the solubility of gaseous reactants such as propylene in the solvent and hydrogen peroxide.

The process of this invention may be carded out in a batch, continuous, or semi-continuous manner using any appropriate type of reaction vessel or apparatus such as a fixed bed, transport bed, fluidized bed, stirred slurry, or CSTR reactor in a monophase or biphase system. Known methods for conducting metal-catalyzed epoxidations of olefins using an active oxygen oxidizing agent will generally also be suitable for use in this process. Thus, the reactants may be combined all at once or sequentially. For example, the oxidizing agent may be added incrementally to the reaction zone. The oxidizing agent could also be generated in situ within the same reactor zone where epoxidation is taking place. Once the epoxidation has been carried out to the desired degree of conversion, the epoxide product may be separated and recovered from the reaction mixture using any appropriate technique such as fractional distillation, extractive distillation, liquid-liquid extraction, crystallization, or the like. After separating from the epoxidation reaction mixture by any suitable method such as filtration, the recovered catalyst may be economically reused in subsequent epoxidations. Where the catalyst is deployed in the form of a fixed bed, the epoxidation product withdrawn as a stream from the epoxidation zone will be essentially catalyst free with the catalyst being retained within the epoxidation zone. In certain embodiments of the instant process where the epoxide is being produced on a continuous basis, it may be desirable to periodically or constantly regenerate all or a portion of the used titanium-containing molecular sieve catalyst in order to maintain optimum activity and selectivity. Suitable regeneration techniques include, for example, treating the catalyst with solvent, calcining the catalyst, and/or contacting the catalyst with an ammonium, alkali metal or alkaline earth compound. Any unreacted olefin or oxidizing agent may be similarly separated and recycled. Alternatively, the unreacted oxidizing agent (especially if present at concentrations too low to permit economic recovery) could be thermally or chemically decomposed into non-peroxy species. In certain embodiments of the process where the oxidizing agent is hydrogen peroxide generated by molecular oxygen oxidation of a secondary alcohol, the crude epoxidation reaction mixture will also contain a secondary alcohol and a ketone corresponding to the secondary alcohol. After separation of the epoxide from the secondary alcohol and the corresponding ketone, the ketone may be converted back to secondary alcohol by hydrogenation. For example, the ketone may be reacted with hydrogen in the presence of a transition metal hydrogenation catalyst such as a Raney nickel, copper chromite, ruthenium, or supported palladium catalyst. Hydrogenation reactions of this type are well known to those skilled in the art. The secondary alcohol may also be dehydrated using known methods to yield valuable alkenyl products such as styrene.

The titanium-containing molecular sieve described herein, in addition to being a useful epoxidation catalyst, also has utility as an ion exchanger, a shape-selective separation medium, or a catalyst for other hydrocarbon conversion processes, including, for example: cracking, selectoforming, hydrogenation, dehydrogenation, oligomerization, alkylation, isomerization, dehydration, hydroxylation of olefins or aromatics, alkane oxidation, reforming, disproportionation, methanation, and the like. The molecular sieve of this invention is particularly useful for catalyzing the same reactions wherein titanium silicalites (also referred to as titanium silicates) have heretofore been employed. Illustrative applications of this type are as follows:

a) A process for the manufacture of a ketone oxime which comprises reacting a ketone such as cyclohexanone with ammonia and hydrogen peroxide in the liquid phase at a temperature of from 25° C. to 150° C. in the presence of a catalytically effective amount of the titanium-containing molecular sieve. Reactions of this type are well known in the art and suitable conditions for carrying out such a synthetic transformation in the presence of a titanium silicalite catalyst are described, for example, in U.S. Pat. No. 4,745,221, Roffia et al., "Cyclohexanone Ammoximation: A Breakthrough in the 6-Caprolactam Production Process", in *New Developments in Selective Oxidation*, Centi et al, eds., pp. 43–52 (1990), Roffia et al., "A New Process for Cyclohexanonoxime", *La Chimica & L'Industria* 72, pp. 598–603 (1990), U.S. Pat. No. 4,894,478, U.S. Pat. No. 5,041,652, U.S. Pat. No. 4,794,198, Reddy et al., "Ammoximation of Cyclohexanone Over a Titanium Silicate Molecular Sieve", *J. Mol. Cat.* 69, 383–392 (1991), European Pat. Pub. No. 496,385, European Pat. Pub. No. 384,390, and U.S. Pat. No. 4,968,842, (the teachings of the foregoing publications are incorporated herein by reference in their entirety).

(b) A process for oxidizing a paraffinic compound (i.e., a saturated hydrocarbon) comprising reacting the paraffinic compound at a temperature of from 25° C. to 200° C. with hydrogen peroxide in the presence of a catalytically effective amount of the titanium-containing molecular sieve. Reactions of this type are well known in the art and suitable conditions for carrying out such a synthetic transformation in the presence of a titanium silicalite are described, for example, in Huybrechts et al., *Nature* 345,240 (1990), Clerici, *Appl. Catal.* 68, 249 (1991), and Tatsumi et al., *J. Chem. Soc. Chem. Commun.* 476 (1990), Huybrechts et al., *Catalysis Letters* 8, 237–244 (1991), the teachings of which are incorporated herein by reference in their entirety.

(c) A process for hydroxylating an aromatic hydrocarbon (e.g., phenol) comprising reacting the aromatic compound at a temperature of from 50° to 150° C. with hydrogen peroxide in the presence of a catalytically effective amount of the titanium-containing molecular sieve to form a phenolic compound (e.g., cresol). Reactions of this type are well known in the art and suitable conditions for carrying out such a synthetic transformation in the presence of a titanium silicalite catalyst are described, for example, in U.S. Pat. No. 4,396,783, Romano et al., "Selective Oxidation with Ti-silicalite", *La Chimica L'Industria* 72, 610–616 (1990), Reddy et al., *Applied Catalysis* 58, L1–L4 (1990), (d) A process for isomerizing an aryl-substituted epoxide to the corresponding beta-phenyl aldehyde comprising contacting the aryl-substituted epoxide with a catalytically effective amount of the titanium-containing molecular sieve at a temperature of from 25° C. to 150° C. See, for example, U.S. Pat. No. 4,495,371 (incorporated herein by reference in its entirety).

(e) A process for oxidizing a vinyl benzene compound to the corresponding beta-phenyl aldehyde comprising reacting the vinyl benzene compound with hydrogen peroxide at a temperature of from 20° C. to 150° C. in the presence of the titanium-containing molecular sieve. See, for example, U.S. Pat. No. 4,609,765 (incorporated herein by reference in its entirety).

(f) A process for synthesizing an N, N-dialkyl hydroxylamine comprising reacting the corresponding secondary dialkyl amine with hydrogen peroxide in the presence of the titanium-containing molecular sieve. See, for example, U.S. Pat. No. 4,918,194 (incorporated herein by reference in its entirety).

(g) A process for oxidizing an aliphatic alcohol comprising reacting the aliphatic alcohol with hydrogen peroxide in the presence of the titanium-containing molecular sieve at a temperature of from 25° C. to 150° C. to form the corresponding ketone or aldehyde of said aliphatic alcohol. See, for example, U.S. Pat. No. 4,480,135 (incorporated herein by reference in its entirety).

(h) A process for synthesizing a glycol monoalkyl ether comprising reacting an olefin, an aliphatic alcohol, and hydrogen peroxide in the presence of the titanium-containing molecular sieve at a temperature of from 25° C. to 150° C. See, for example, U.S. Pat. No. 4,476,327 (incorporated herein by reference in its entirety).

From the foregoing description, one skilled in the art can readily ascertain the essential characteristics of this invention, and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

This example illustrates the preparation of a titanium-containing molecular sieve essentially free of framework aluminum and having a framework structure isomorphous to zeolite beta, wherein a benzyl-substituted ammonium species is utilized as a template.

The template, 4,4'-trimethylene bis (N-benzyl N-methyl piperidinium) dihydroxide, was prepared as follows: To 800 mL of ethyl acetate was added 25 g (0.105 mole) of 4,4'-trimethylene bis (1-methyl piperidine). To this solution was then added dropwise under a gently flowing nitrogen stream 36.8 g (0.215 mole) benzyl bromide. A white precipitate soon formed and the resulting mixture was stirred overnight under nitrogen. The solid precipitate was recovered, washed well with ethyl acetate, and then re-slurried in pentane. After recovering the precipitate a second time and washing with pentane, the product was dried under vacuum at 30° C. for 48 hours. The yield of the dibromide salt was nearly quantitative. The dihydroxide salt was prepared by ion-exchanging about 50 mmol of the dibromide salt using 300 g BioRad Ag 1-X8 anion exchange resin. The resultant diquaternary ammonium species was obtained as a nearly colorless aqueous solution after low temperature removal of water to concentrate the solution.

To 30 g (0.144 mol) tetraethylorthosilicate was added dropwise 0.72 g 0.05M aqueous HCl. The resulting clear solution was stirred for two hours at room temperature under a gentle stream of nitrogen. After this time, 30 mL absolute ethanol was added followed by a dropwise addition of 1.53 g (0.045 mole) titanium tetra-n-butoxide in 20 mL isopropanol. Thereafter, 2 g of a 1.27N solution of the trimethylene bis (benzyl methyl piperidine) dihydroxide was added dropwise. The solution was dried at 110° C. overnight yielding 13.3 g of dry white powder. A diffuse-reflective UV spectrum of the dried cogel exhibited two strong absorbances at 216 and 235 nm.

An additional portion (17 g) of the aforementioned template solution was combined with 4 g doubly distilled/deionized water. Using a wetness impregnation method, the resulting diluted template solution was added dropwise to the dried cogel. The amount of solution was somewhat greater than was required for incipient wetness, resulting in the production of a very runny slurry. The molar gel composition for the slurry was:

0.144 Si:0.045 Ti:0.012 DQ:0.024 OH:0.973 $H_2O$

Si/Ti=32; DQ/Si=0.084; OH/Si=0.167; $H_2O$/Si=6.8

DQ=dication portion of the diquaternary ammonium species

The slurry was placed into teflon-lined Parr reactors and heated static at 135° C. for 8 days (shorter reaction times were found to yield partially amorphous products). After this time, the solids were recovered, washed with water, and then dried at 110° C. overnight. Powder XRD analysis confirmed that the dried titanium-containing molecular sieve had a zeolite beta structure with no detectable contamination from other phases such as ZSM-12. TGA analysis indircted that 26.1% weight loss at 800° C. occurred due to loss of the template, corresponding to 3.3 template molecules per 64 Ti atoms. DSC analysis showed a single exotherm (to 700° C.) centered at 432° C. with an onset at 382° C. According to the literature [van der Waal et al., *J. Chem. Soc., Chem., Commun.* 1241–1242 (1994)], silica-boron zeolite beta contains substantial amounts of coke when calcined at 400° C., with calcination at 700° being required to remove the coke. Such calcination, however, causes a loss in crystallinity. In contrast, the titanium-containing zeolite beta prepared in accordance with the present invention can be calcined at 550° C. for 8 hours in dry air with complete removal of all template (as evidenced by elemental analysis). XRD of the calcined material (FIG. 1) showed no loss of crystallinity.

Elemental analysis of the calcined material showed 32% Si, 2.0% Ti, <100 ppm Al, 0.025% Na (Si/Ti=27.3, Si/Al>3500). The calcined material had a micropore volume of 0.269 mL/g ($N_2$ B.E.T. measurement), in good agreement with the value of 0.266 mL/g reported for all-silica zeolite beta. Toluene adsorption was 230 mg/g as compared to 170 mg/g for H—Al/beta, suggesting a more hydrophobic environment. DR-UV spectroscopy showed a strong absorbance at 216 nm with a second smaller peak at 232 nm. A small peak at 330 nm was present, evidencing a minor degree of anatase contamination. IR spectroscopy of the calcined molecular sieve exhibited a moderately strong resonance at 953 $cm^{-1}$, which has been assigned to a perturbation in the $SiO_4$ network due to the absorption of $TiO_4$ units.

Figure 3:
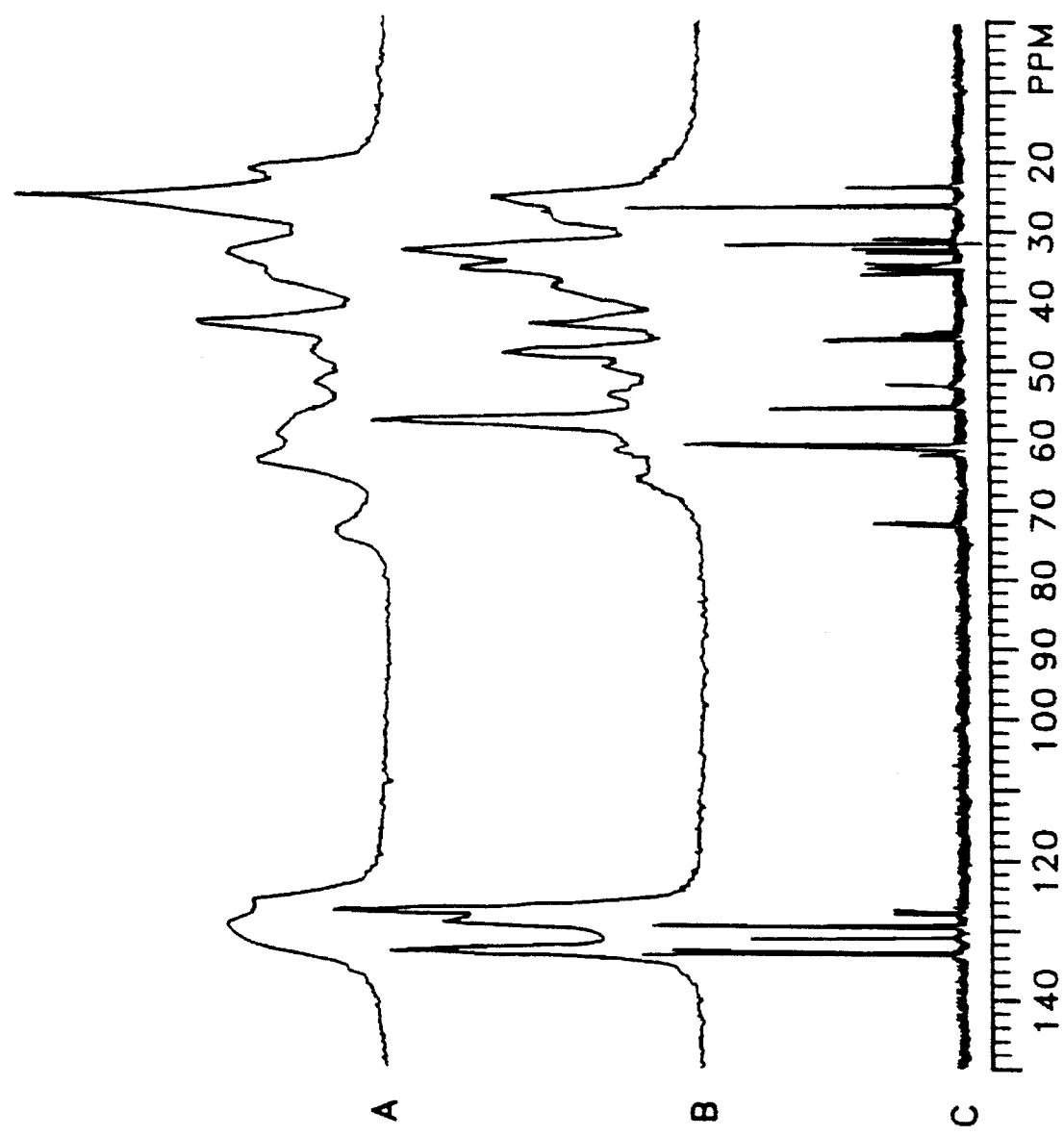
FIG. 3 comprises the $^{13}C$ NMR spectra of a benzyl-substituted ammonium species in various environments.

$^{29}Si$ MAS-NMR of the as-synthesized (uncalcined) molecular sieve indicated that the diquaternary ammonium template remained intact inside the lattice framework during hydrothermal synthesis. The $^{13}C$ MAS-NMR spectrum of the as-synthesized molecular sieve is shown as A in FIG. 3, together with the $^{13}C$ MAS-NMR spectrum of 4,4'-trimethylene bis(benzyl methyl piperidenium) dibromide (B in FIG. 3) and the solution $^{13}C$ MAS-NMR spectrum of the dibromide in $d_6$-acetone (C in FIG. 3), which further confirms the presence of the diquaternary ammonium species. $^{13}C$ MAS-NMR of the calcined molecular sieve showed a Q3 band (−101 ppm) about 2.5 times that of the Q4 band (−110 ppm), which is similar to the ratio seen for TS-1 (MFI) titanium silicalites. This indicates that the molecular sieve of this invention does not contain an appreciably greater number of defect of silanol (SiOH) sites than TS-1. SEM analysis of the as-synthesized molecular sieve showed homogeneous, small (submicron) particles of spherical morphology with no evidence of amorphous material.

A calcined titanium-containing molecular sieve having a zeolite beta structure prepared as described hereinabove was found to be active as an epoxidation catalyst using either aqueous hydrogen peroxide or organic hydroperoxides such as t-butyl hdyroperoxide. These results are summarized in Tables I and II. For example, using 1-hexene as a substrate at 60° C. with 50% $H_2O_2$ (olefin: $H_2O_2$=3.3) in methanol solvent, there was analyzed after one hour 27% conversion, 37% selectivity (based on $H_2O_2$) to the epoxide with 12% selectivity to the methyl ethers. After 3 hours there was seen 71% conversion with 17% epoxide and 11% glycol methyl ether selectivity (epoxide/glycols ratio=3.2). Using unneutralized Ti—Al/β (i.e., a zeolite beta containing Si, Ti, and Al in its framework structure), in contrast, near 100% selectivity to ring-opened by-products is obtained under similar conditions. To determine the effect of water, the reaction solution was first dried with magnesium sulfate. Under conditions otherwise identical to those previously described, there was analyzed after 1 hour 40% $H_2O_2$ conversion with 40% selectivity to epoxide and only 4% selectivity to ring-opened by-products (epoxide/glycols ratio=10).

Even better results were attained using t-butyl hydroperoxide (90% solution in t-butyl alcohol/water) as an oxidizing agent. Using ethylbenzene as solvent and 1-octene as the olefin, at 90° C. them was analyzed after 1 hour 78% TBHP conversion with 68% selectivity to the epoxide and less than 1% selectivity to glycols. By way of comparison, the use of unneutralized Ti—Al/β under similar conditions (1.5 hr reaction time) led to 58% TBHP conversion, only 38% selectivity to epoxide, and 61% selectivity to glycols.

EXAMPLE 2

This example demonstrates an alternative method of preparing a titanium-containing molecular sieve in accordance with the present invention.

Calcined zeolite beta (5 g; Conteka 41-89-001) having a $SiO_2$:$Al_2O_3$ ratio of 24 is added to 500 ml of 13N nitric acid.

The resulting suspension is heated at 80° C. for four hours with stirring. The suspended solids are recovered by filtration and retreated twice in the same manner with fresh portions of 13N nitric acid. After recovering by filtration, the solids are washed well with deionized water, and dried at 95° C. overnight to provide a dealuminated zeolite beta having a Si/Al molar ratio of 940.

Figure 2:
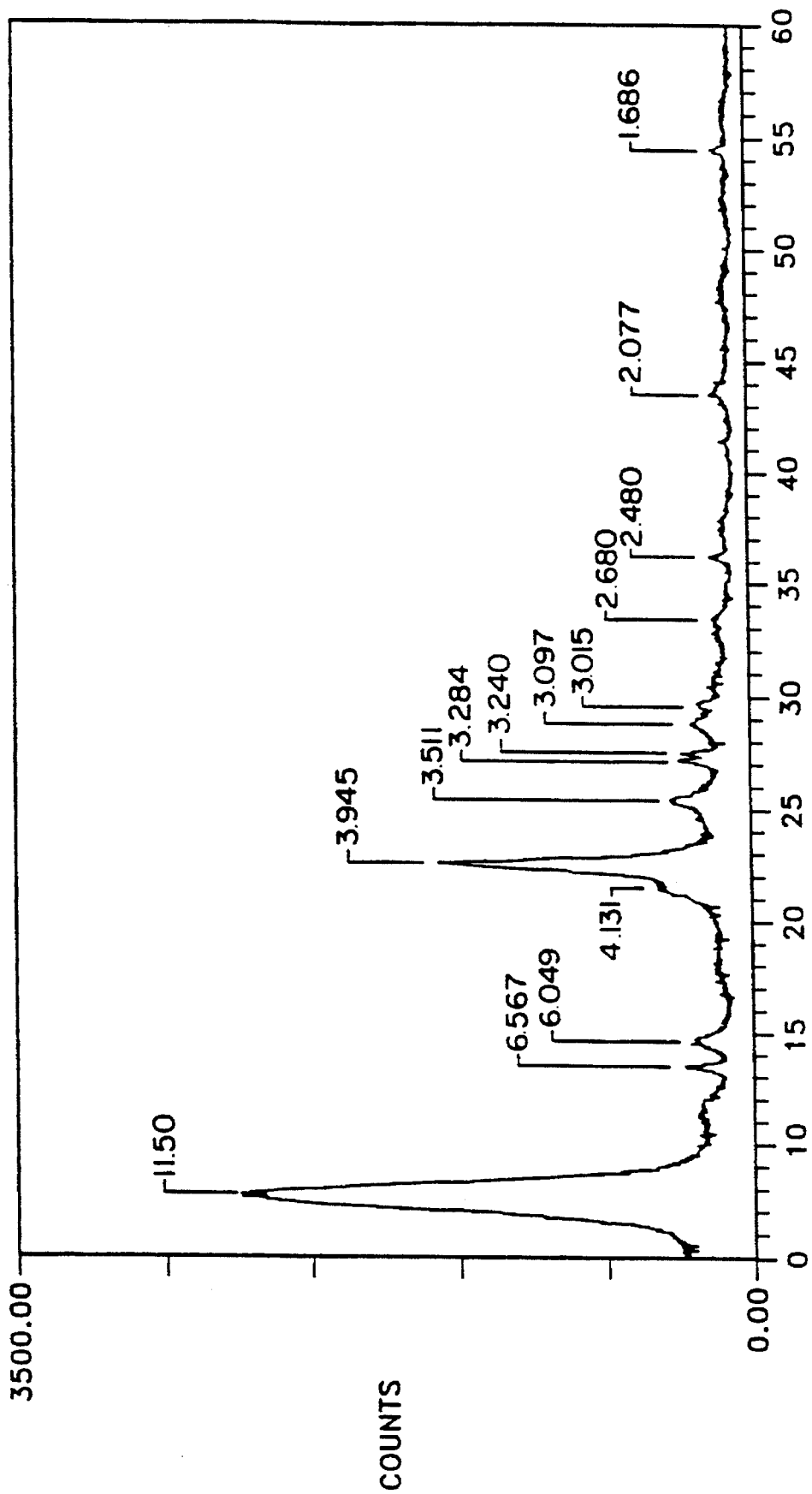
FIG. 2 is an x-ray powder diffraction pattern of the titanium-containing molecular sieve prepared using the procedure of Example 2.

The dealuminated zeolite beta is added to a fitted quartz tube. The tube is loaded vertically in a furnace and a slow (100 cc/min) nitrogen flow initiated. The sample is heated at 400° C., then heated at 600° C. and the nitrogen flow increased to 300 cc/min. Once the temperature has stabilized at 600° C., the sample is treated with titanium tetrachloride for eight hours by sparging the nitrogen feed through a warmed (40° C.) $TiCl_4$ solution. After this time, $TiCl_4$ treatment is discontinued and nitrogen flow through the sample continued at 600° C. for an additional hour. The sample is cooled to room temperature overnight with continuous nitrogen flow. The cooled sample is treated with a 1M aqueous solution of ammonium nitrate at 80° C. for four hours. The sample is recovered by filtration, washed well with water, dried at 95° C. and then calcined at 550° C. for 6 hours to yield a titanium-containing molecular sieve having a very low level of aluminum. Raman spectroscopy and $^{29}Si$ and $^{27}Al$ MAS NMR also confirmed that near complete dealumination takes place and that titanium is inserted into the framework of the zeolite. The x-ray powder diffraction pattern of the titanium-containing molecular sieve is shown in FIG. 2 and summarized in Table III. Elemental analysis indicated that the molecular sieve contained 200–300 ppm aluminum.

The titanium-containing molecular sieve thus obtained is evaluated as a catalyst for the hydrogen peroxide epoxidation of 1-hexene using the following conditions: 60° C., 12.2 g methanol (solvent), 16.5 mmol 1-hexene, 4.5 mmol hydrogen peroxide, 0.10 g catalyst.

The results of this evaluation are shown in Table IV. Example 2-A shows that good epoxide selectivity can be achieved without modification of the catalyst with Group IA or Group IIA cations, due (it is believed) to the extremely low aluminum content of the catalyst. The activity of the catalyst was quite high, with over 90% conversion of hydrogen peroxide being attained in just one hour. When the catalyst was washed with 0.5% sodium acetate (Example 2-B), a somewhat lower initial rate of hydrogen peroxide reaction was observed together with improved selectivity. Example 2-C demonstrates that the titanium-containing molecular sieve which has been treated with sodium acetate also performs quite satisfactorily if alpha-methyl benzyl alcohol rather than methanol is used as a solvent for epoxidation. In contrast, titanium silicalite having a TS-1 structure exhibited little activity in an alpha-methyl benzyl alcohol medium (Example 2-D).

EXAMPLE 3

The following example illustrates an alternative method of preparing the Al-free titanium-containing molecular sieve of this invention using a diquaternary ammonium species as a template.

A solution of 4,4'-trimethylene bis (N-benzyl N-methyl piperidinium) dihydroxide was prepared as in Example 1 from 30 g of the corresponding dibromide salt. Tetraethylorthosilicate (30 g; 0.144 mol) was partially hydrolyzed by adding dropwise into 50 ml of 0.49N (by hydroxide) aqueous template. To this homogeneous solution was added titanium tetrabutoxide (1.74; 0.00511 mol) in 5 g (0.024 mol) tetraethylorthosilicate. To the resulting turbid mixture was added the remaining portion of the template solution (from 0.0517 mol). After stirring at room temperature for two hours, the ethanol formed during hydrolysis was removed by evaporation and the precursor gel aged overnight. The precursor gel had the following composition:

$$TiO_2:10 \text{ template}:33 \text{ } SiO_2:800 \text{ } H_2O$$

The clear precursor gel was loaded into teflon-lined reactors and heated in a shaker oven at 135° C. for nine days. The crystalline solids thereby obtained exhibited an XRD pattern characteristic of a beta framework structure. After calcination, the molecular sieve exhibited two bands in the UV/VIS spectrum at 233 nm and 214 nm with absorbances at 0.420 and 0.391 respectively. Elemental analysis confirmed presence of 1.9 wt. % Ti, 0.005 wt. % Al, and 43 wt. % Si.

Epoxidation of 1-hexene using hydrogen peroxide and the calcined molecular sieve at 60° C. gave 44% conversion after one hour with a selectivity of 45.3% based on hydrogen peroxide. The organic products formed were 73.8% 1-hexene oxide and 26.2% glycol ethers. A sample taken after six hours showed 100% conversion with a selectivity of 31% based on hydrogen peroxide. The organic products formed were 42% (by weight) 1-hexene oxide and 58% glycol ethers.

TABLE I

| Oxidizing Agent | Form | Time, hr. | Oxidizing Agent % Conversion | % Epoxide Selectivity[1] | % Total Glycol Selectivity[1] |
|---|---|---|---|---|---|
| $H_2O_2$ | 50% solution | 1 | 27 | 37 | 12 |
|  |  | 3 | 71 | 17 | 11 |
| $H_2O_2$ | 50% dried | 1 | 40 | 40 | 4 |
|  |  | 2 | 60 | 44 | 12 |
| TBHP | 90% solution | 1 | 74 | 62 | 6 |
| TBHP | 90% dried | 1 | 78 | 68 | <1 |

[1]based on oxidizing agent
Conditions:
(a) $H_2O_2$ Examples — 6.3 g MeOH, 4.0 mmol $H_2O_2$, 15 mmol 1-hexene, 60° C., 0.15 g catalyst
(b) TBHP Examples, 6.0 g ethylbenzene, 3.8 mmol TBHP, 15 mmol 1-octene, 90° C., 0.15 g catalyst

TABLE II

| Catalyst | Olefin | Oxidizing Agent | Time, hr. | Temp., °C. | Oxidizing Agent, % Conversion | % Epoxide Selectivity[3] | % Total Glycol & Other Selectivity |
|---|---|---|---|---|---|---|---|
| Ti/β[1] | 1-hexene | $H_2O_2$ | 3 | 60 | 71 | 17 | 11 |
| Ti—Al/β[2] | 1-hexene | $H_2O_2$ | 3 | 80 | 80 | 9.6 | 64 |
| Ti/β[1] | 1-octene | TBHP | 1 | 90 | 78 | 68 | <1 |
| Ti—Al/β[2] | 1-octene | TBHP | 1.5 | 90 | 58 | 38 | 61 |

[1] catalyst of this invention
[2] comparative example; unneutralized catalyst prepared in accordance with the disclosure of Camblor et al., J. Chem. Soc., Chem. Commun. pp. 589–590 (1992), Zeolites 13, pp. 82–87 (1993), and ES 2037596
[3] based on oxidizing agent Conditions:
(a) $H_2O_2$ Examples — 6.3 g MeOH, 4.0 mmol $H_2O_2$ 15 mmol 1-hexene, 60° C., 0.15 catalyst
(b) TBHP Example — 6.0 g ethylbenzene, 3.8 mmol TBHP, 15 mmol 1-octene, 90° C., 0.15 g catalyst; $CF_3CH_2OH$ is given as the solvent using Ti—Al/β catalyst since this solvent gives the best results according to Sato et al., J. Chem. Soc., Chem. Commun. 1887–1888 (1994).

TABLE III

| d (angstroms) | Relative Intensity |
|---|---|
| 11.50 | vs |
| 6.57 | mw |
| 6.05 | mw |
| 4.13 | w |
| 3.95 | s |
| 3.51 | mw |
| 3.28 | mw |
| 3.24 | mw |
| 3.19 | w |
| 3.02 | w |
| 2.68 | w |
| 2.48 | w |
| 2.08 | w |
| 1.69 | w | d = interplanar distance
vs = very strong
s = strong
mw = medium weak
w = weak

TABLE IV

| Example | Solvent | Catalyst Treatment | Time, hr | $H_2O_2$ Conversion, % | Epoxide Selectivity, %[a] | Glycol Ether Selectivity, %[a] | Hexene Conversion % | Epoxide/ Glycol Ether Ratio |
|---|---|---|---|---|---|---|---|---|
| 2-A | methanol | none | 1 | 93 | 58 | 1.7 | 19 | 3 |
|  |  |  | 6 | 96 | 52 | (+17% other) 3 (+39% other) | 31 | 1 |
| 2-B | methanol | 0.5% NaOAc | 1 | 68 | 75 | 5 | 16 | 15 |
|  |  |  | 6 | 97 | 63 | 19 | 23 | 4 |
| 2-C | alpha methyl benzyl alcohol | 0.5% NaOAc | 1 | 98 | 68 | <2 | 18.4 | >50 |
| 2-D[c] | alpha methyl benzyl alcohol | —[b] | 1 | no reaction | — | — | — | — |

[a] based on hydrogen peroxide
[b] TS-1 catalyst (U.S. Pat. No. 4,410,501)
[c] comparative example

We claim:

1. A method of making a crystalline titanium-containing molecular sieve characterized by a framework structure isomorphous to zeolite beta, and comprised of Si and Ti, but essentially free of framework Al, comprising:

(a) reacting a hydrolyzable silicon compound and a hydrolyzable titanium compound with water under acidic conditions to form a solubilized partial hydrozylate characterized by the absence of precipitated silicon dioxide and titanium dioxide;

(b) contacting the solubilized partial hydrozylate with an amount of a benzyl-substituted ammonium species effective to catalyze further hydrolysis to form a solid amorphous $SiO_2$—$TiO_2$ cogel;

(c) contacting the solid amorphous $SiO_2$—$TiO_2$ cogel with a solution of the benzyl-substituted ammonium species in a solvent to form an impregnated cogel; and (d) heating the impregnated cogel at a temperature of from 120° C. to 160° C. for a time sufficient to form the crystalline titanium-containing molecular sieve.

2. The method of claim 1 wherein the crystalline titanium-containing molecular sieve is calcined following step (d).

3. The method of claim 1 wherein the hydrolyzable silicon compound is a tetraalkyl orthosilicate.

4. The method of claim 1 wherein the hydrolyzable titanium compound is a titanium tetraalkoxide.

5. The method of claim 1 wherein the total amount of benzyl-substituted ammonium species in steps (b) and (c) is within 50% of the amount needed to occupy the pore volume of the solid amorphous $SiO_2$—$TiO_2$ cogel.

6. The method of claim 1 wherein the hydrolyzable silicon compound is reacted first with water prior to reacting the hydrolyzable titanium compound with water.

7. The method of claim 1 wherein the amount of solvent is sufficient to dissolve the benzyl-substituted ammonium species without forming a slurry of the impregnated cogel in said solvent.

8. The method of claim 1 wherein the benzyl-substituted ammonium species is a diquaternary ammonium species and the impregnated cogel has a composition expressed in terms of molar ratios within the following ranges:

| | |
|---|---|
| $SiO_2/TiO_2$ | 5–200 |
| $X^-/SiO2$ | 0.02–1 |
| $H_2O/SiO_2$ | 0.1–10 |
| $M^+/SiO_2$ | $\leq 0.5$ |
| $DQ^{2+}/SiO_2$ | 0.005–2.0 | wherein $M^+$ is an alkali metal cation, $X^-$ is the anion component of the diquaternary ammonium species, and $DQ^+$ is the dication component of the diquaternary ammonium species.

9. The method of claim 1 wherein each nitrogen atom of the benzyl-substituted ammonium species bears a single benzyl substituent.

10. The method of claim 1 wherein the crystalline titanium-containing molecular sieve is calcined and the calcined crystalline titanium-containing molecular sieve has the empirical formula $$SiO_2:TiO_2$$

wherein y is from 0.01 to 0.25.

11. The method of claim 1 wherein the benzyl-substituted ammonium species has the structure

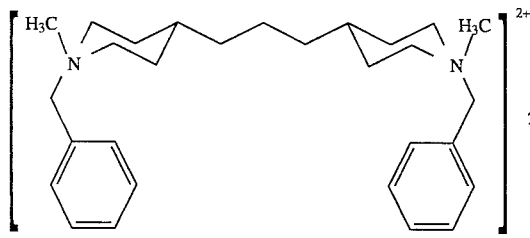

wherein X is halide or hydroxide.

12. A method of preparing a crystalline titanium-containing molecular sieve characterized by a framework structure isomorphous to zeolite beta and comprised of Si and Ti, but essentially free of framework Al, said method comprising forming a mixture of a hydrolyzable silicon compound, a hydrolyzable titanium compound, and a benzyl-substituted ammonium species wherein each nitrogen atom bears a single benzyl substituent and subjecting said mixture to hydrothermal treatment at a temperature of from 100° to 200° C. for a time effective to form the crystalline titanium-containing molecular sieve.

13. The method of claim 12 wherein the hydrolyzable silicon compound is tetraalkylorthosilicate.

14. The method of claim 12 wherein the hydrolyzable titanium compound is a titanium tetraalkoxide.

15. The method of claim 12 wherein the benzyl-substituted ammonium species is a diquaternary species.

16. The method of claim 12 wherein the crystalline titanium-containing molecular sieve is calcined.

17. The method of claim 12 wherein the molar ratio of hydrolyzable silicon compound to hydrolyzable titanium compound is from 5 to 200.

18. The method of claim 12 wherein the molar ratio of hydrolyzable silicon compound to benzyl-substituted ammonium species is from 0.03 to 2.0.

19. The method of claim 12 wherein the hydrolyzable titanium compound is titanium tetra-n-butoxide.

20. The method of claim 12 wherein the benzyl-substituted ammonium species has the structure

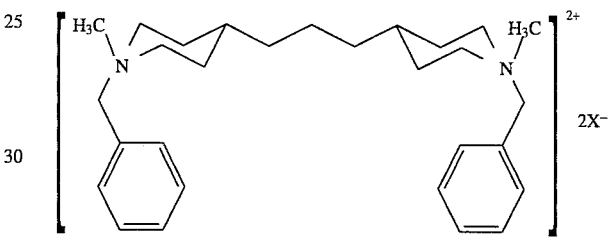

wherein X is halide or hydroxide.

21. The method of claim 12 wherein said mixture is formed in an aqueous medium under conditions effective to accomplish hydrolysis of the hydrolyzable titanium compound and hydrolyzable silicon compound.

22. The method of claim 12 wherein the hydrolyzable silicon compound is partially hydrolyzed prior to being combined with the hydrolyzable titanium compound.

23. A crystalline titanium-containing molecular sieve characterized by a framework structure isomorphous to zeolite beta, and comprised of Si and Ti, but essentially free of framework Al prepared by the method of claim 1 or 12.

* * * * *